(12) United States Patent
Calender

(10) Patent No.: US 8,460,265 B1
(45) Date of Patent: Jun. 11, 2013

(54) WASHABLE FEMALE UNDERGARMENT

(76) Inventor: Vida Langdon Calender, Hamilton, OH (US)

( * ) Notice: Subject to any disclaimer, the term of this patent is extended or adjusted under 35 U.S.C. 154(b) by 447 days.

(21) Appl. No.: 12/802,549

(22) Filed: Jun. 9, 2010

Related U.S. Application Data

(60) Provisional application No. 61/268,201, filed on Jun. 10, 2009.

(51) Int. Cl.
- *A61F 13/15* (2006.01)
- *A41B 9/02* (2006.01)
- *A41B 9/04* (2006.01)

(52) U.S. Cl.
USPC .......... 604/396; 604/385.22; 604/385.15; 604/385.16; 604/385.21; 2/401; 2/406; 2/407

(58) Field of Classification Search
USPC .......... 604/385.22, 385.15, 385.16, 385.21, 604/396; 2/401, 406, 407
See application file for complete search history.

(56) References Cited

U.S. PATENT DOCUMENTS

| | | | |
|---|---|---|---|
| 4,244,367 A | 1/1981 | Rollenhagen | |
| 4,813,950 A | 3/1989 | Branch | |
| 5,241,710 A | 9/1993 | Lockhart | |
| 5,546,607 A | 8/1996 | Roberts | |
| 6,848,121 B1 | 2/2005 | Halid | |
| 2002/0007171 A1 | 1/2002 | McMahon-Ayerst | |
| 2002/0016580 A1 | 2/2002 | Wada et al. | |
| 2004/0230175 A1 | 11/2004 | Rainville-Lonn et al. | |
| 2004/0236300 A1* | 11/2004 | Gibbs et al. | 604/385.24 |
| 2005/0197643 A1 | 9/2005 | Suga et al. | |
| 2005/0203480 A1 | 9/2005 | Chang | |
| 2008/0222781 A1 | 9/2008 | Rhew | |

* cited by examiner

*Primary Examiner* — Jacqueline F. Stephens
(74) *Attorney, Agent, or Firm* — Charles R. Wilson

(57) ABSTRACT

A washable female undergarment is designed for comfort and for alleviating leakage. The undergarment comprises an outer layer of a stretchable fabric, an inner layer of an absorbent fabric, and a main absorbent layer positioned between the inner and outer layers in the crotch area. The three layers are permanently secured together to form a reusable reliant undergarment.

15 Claims, 5 Drawing Sheets

WASHABLE FEMALE UNDERGARMENT

This application claims the benefit of U.S. Provisional Patent Application Ser. No. 61/268,201, filed Jun. 10, 2009.

FIELD OF THE INVENTION

This invention relates to a washable female undergarment. More particularly, the invention relates to a unitary multi-layer washable female undergarment designed to be comfortably worn and capable of absorbing leakage.

BACKGROUND OF THE INVENTION

There are numerous varieties of female undergarments available in the marketplace. Normal use undergarments tend to be made of a light weight shear material and are full-cut, brief-cut, or any of several stylish cuts. Undergarments for menstruating females tend to be made of an absorptive material such as cotton and sometimes are designed to be worn with a sanitary napkin.

There is a need for a washable female undergarment designed primarily to handle minimal leakage as experienced by many at different times. For example, the minimal leakage may occur just prior to and/or after menstruation, while sleeping, or during periods of high activity, e.g. exercising or playing a sport. There is a need as well for such an undergarment to be worn in conjunction with a sanitary napkin during menstruation. That is, it is quite common for sanitary napkins to become displaced while one is sleeping or doing various tasks throughout the day. Regardless of when used, the undergarment must be comfortable to wear and, most importantly, must be reliable.

In accord with this need, there is now provided a comfortable, breathable, washable, multi-layered, protective undergarment to be used by females. It prevents and/or reduces leakage, seepage or bleed-through (also known as spotting) to outer clothing, linens, bedding, furniture, etc., while at the same time providing the maximum level of comfort for the wearer. Multiple layers in a one-piece article are designed to absorb seepage that would otherwise leak through conventional undergarments at any time throughout a month. Possible staining of external materials and/or objects is avoided. The undergarment is comfortable to wear in all respects.

SUMMARY OF THE INVENTION

A washable female undergarment is designed to alleviate leakage which may spot or show on outer worn clothing, bedding, linens and elsewhere. The undergarment comprises an outer layer made of a stretchable fabric which resists water transfer and an inner layer of a soft absorbent fabric which is comfortable to the touch. A main absorbent layer which is sized to fit in a crotch area of the undergarment is permanently secured in place between the outer and inner layers. The female undergarment is comfortable due to the firm fit provided by the stretchable outer layer of fabric and the absorbent inner layer of fabric. It is capable of absorbing leakage from the wearer because of the main absorbent layer and, to a lesser extent, the inner layer's absorbency and outer layer's snug fit.

DETAILED DESCRIPTION OF THE INVENTION

Figure 1:
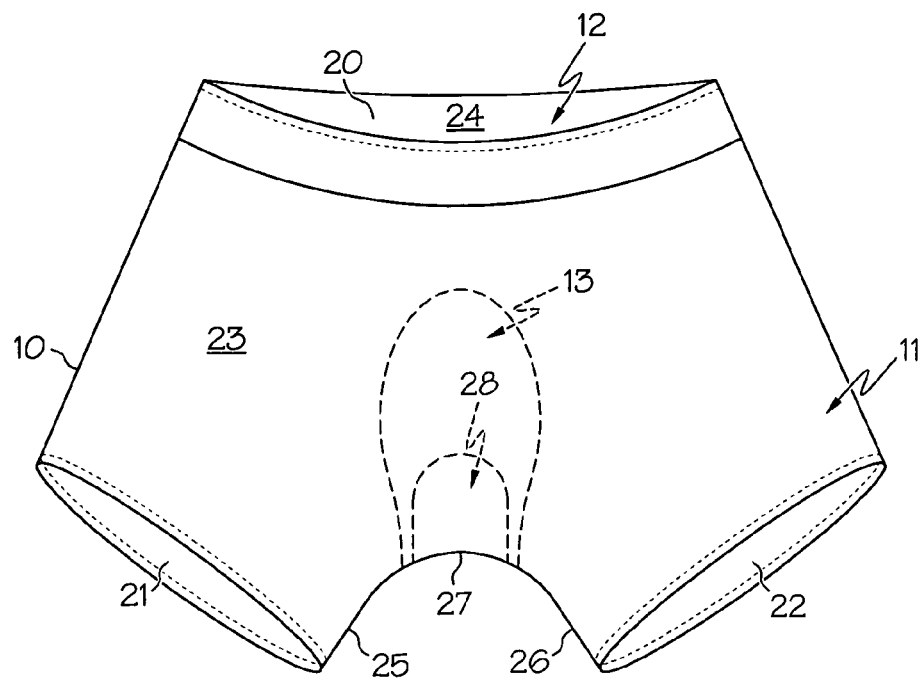
FIG. 1 is a frontal view of the undergarment of the invention showing an outer layer, an inner layer, and, in dotted line form, a main absorbent layer positioned between both inner and outer layers.

The undergarment of the invention is to be worn by females, possibly in conjunction with a sanitary napkin, and/or panty if so desired. It aids in keeping the sanitary napkin in place, as well as provides a means to help with absorption in the event the sanitary napkin becomes displaced. It can also be used by females who may not have started their menstrual cycle yet, but know it is near, and rather than wearing a sanitary napkin, they can use the undergarment instead. The undergarment alleviates inadvertent leakage with a consequence that valuable clothing, bedding, linens, and other items are not ruined, not to mention any embarrassment. It can also be used by people with light incontinence.

The undergarment is described in the following paragraphs and with reference to the drawings. It should be understood the undergarment can be made in any size and any color desired. It is also conducive to being made in various undergarment styles, though the boy shorts style illustrated in the drawings is preferred for reasons discussed below.

Figure 2:
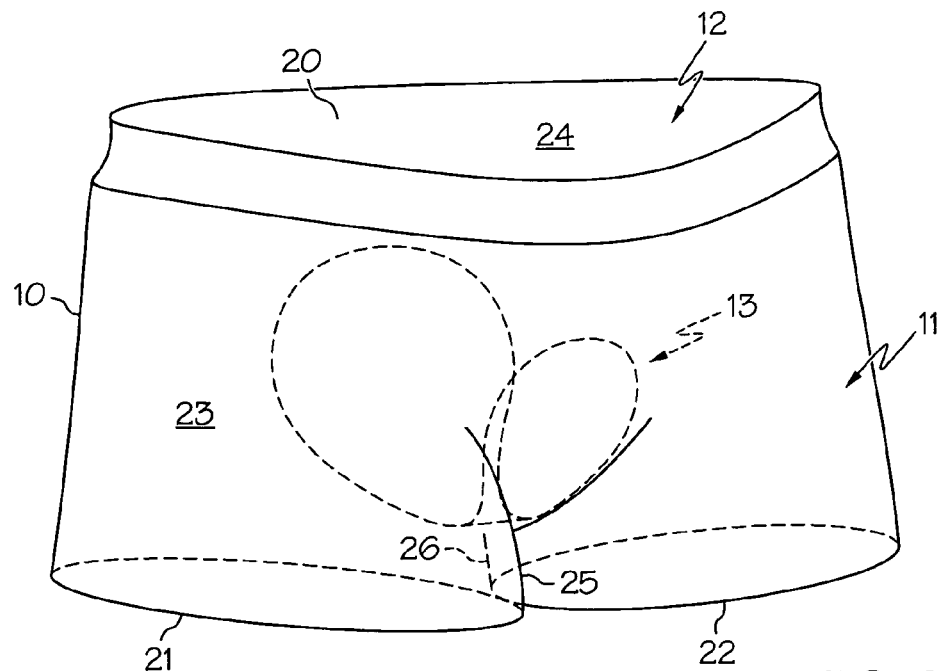
FIG. 2 is a frontal perspective view of the undergarment of FIG. 1.
Figure 3:
FIG. 3 is a frontal view of the outer layer isolated from the undergarment of FIG. 1.
Figure 4:
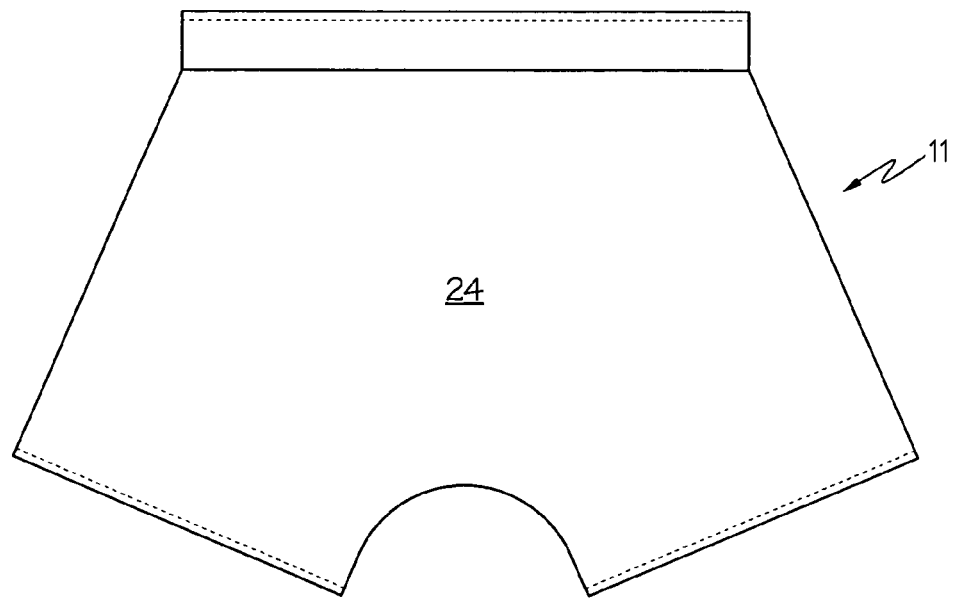
FIG. 4 is a rear view of the outer layer of FIG. 3.

With reference to FIGS. 1 and 2, there is shown an undergarment 10 of the invention comprised of an outer layer 11, an inner layer 12, and a main absorbent layer 13. The three layers are permanently secured to one another to form an article of clothing which is easy to slip into, comfortable to wear, reliable against leakage and, reusable, i.e. washable. The undergarment is considered unitary in that all its individual parts are permanently secured together. The individual layers are discussed in detail below as well as their interaction to form the comfortable and reliable undergarment.

The outer layer 11 is shaped in a manner similar to all undergarments in that it has a waist opening 20 and leg openings 21 and 22. Ideally, it could be cut to shape from a single piece of fabric, but practically it has a front part 23 and a back part 24 each of which are cut and stitched together to form the outer layer 11. The undergarment style shown is termed "boy shorts" because of extended leg sections 25 and 26 which extend about one to two inches onto the wearer's thighs. A crotch part 27 is centered between the leg openings 21 and 22. Loosely defined and as used herein, the crotch is the bottom of wearer's pelvis, where the legs join the torso. A gusset member 28 apparent in FIG. 1 is optionally sewn into the undergarment where the seams of the outer layer come together. As shown, the gusset member 28 is an ovular-shaped piece of fabric.

A stretchable fabric which stretches in multi-directions is used in making the outer layer 11. It must also be washable and breathable. Further, it is water-resistant to help redirect leakage back to the more absorbent inner layer 12. Spandex is highly preferred. The inherent elasticity of spandex fabric provides a firm fitting undergarment which generally moves with the skin of the user. It stays in place when worn. The nature of the undergarment 10 requires a snug fit to keep the main absorbent layer in place to initially receive any leakage. Further, that snug fit discourages any leakage from migrating through the leg openings. The boy shorts style with its extended leg sections 25 and 26 enhance the anti-migration feature of the outer layer 11.

The inner layer 12 is made from a soft absorbent fabric. While the main absorbent layer 13 absorbs most leakage, any excess leakage is easily handled by the inner layer 12. This feature enhances the reliability of the undergarment 10. Cotton fabric is preferred not only because of its absorbency, but also its well recognized comfort to the wearer. It is soft to the touch and breathable. It is also washable.

Figure 5:
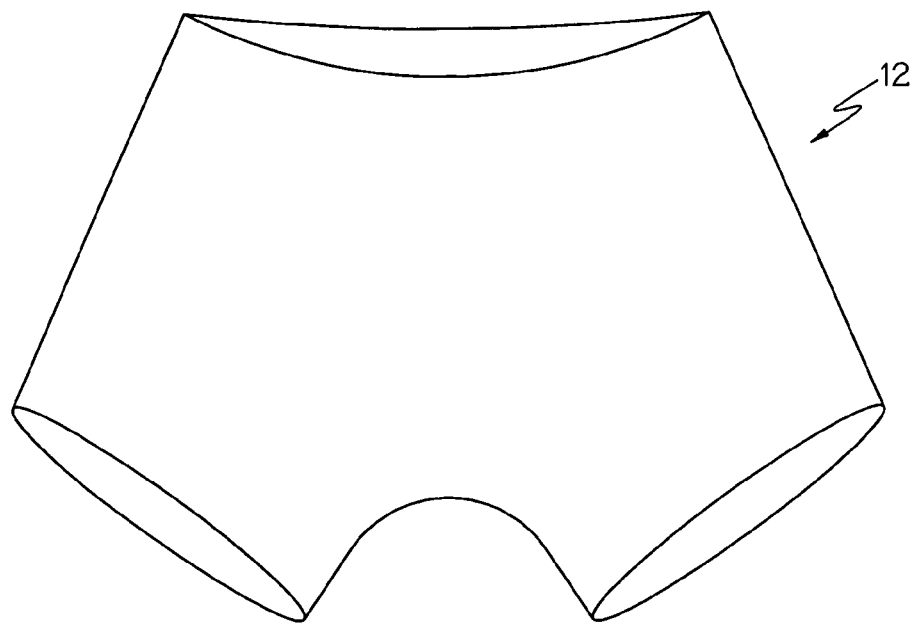
FIG. 5 is a frontal view of the inner layer isolated from the undergarment of FIG. 1.
Figure 6:
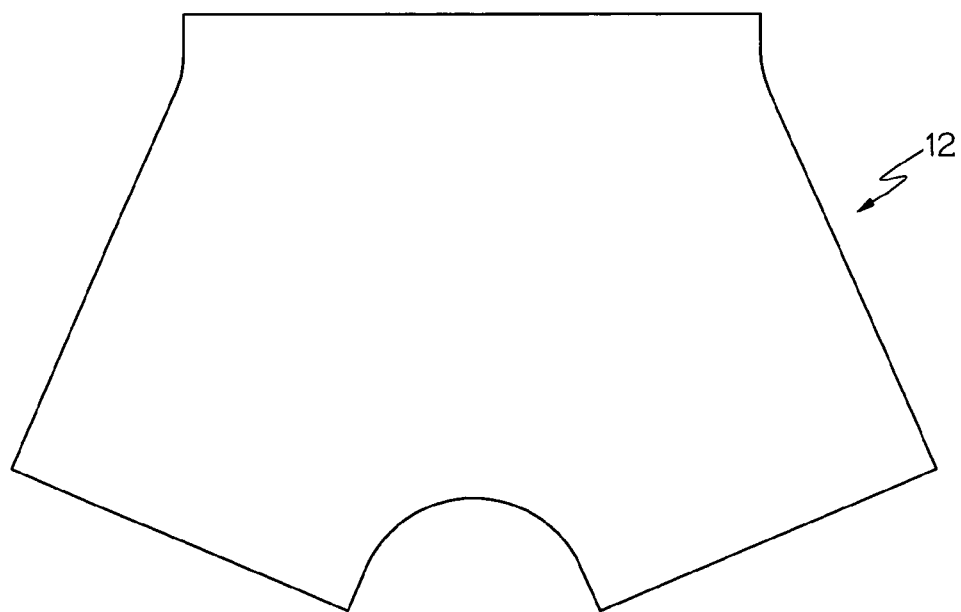
FIG. 6 is a rear view of the inner layer of FIG. 5.
Figure 7:
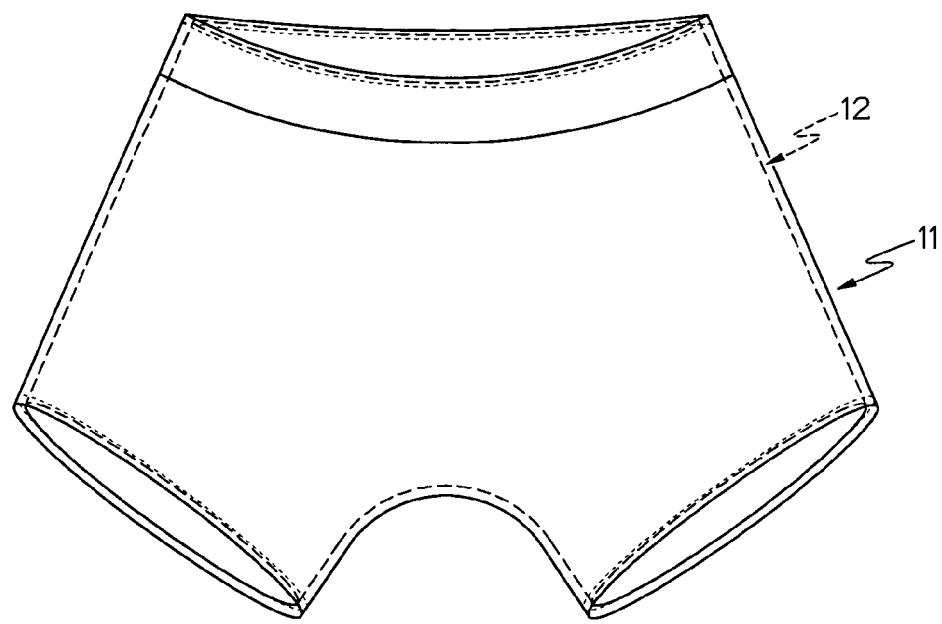
FIG. 7 is a frontal view of the undergarment of FIG. 1 wherein the inner layer is in dotted line form to show its similarity in shape and size to the outer layer.
Figure 8:
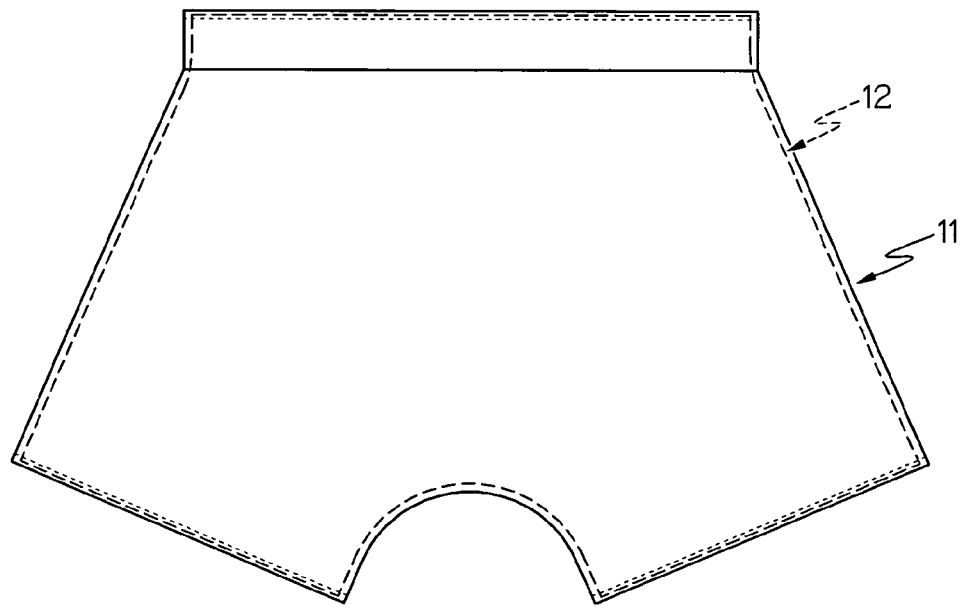
FIG. 8 is a rear view of the undergarment of FIG. 7.

With reference to FIGS. 5 and 6, the inner layer 12 is shaped and sized to fit within the outer layer 11. Necessarily, it is substantially identical in shape and size as the outer layer. It is, practically speaking, cut and stitched to create a waist opening and two leg openings. Now with reference to FIGS. 7 and 8, it is permanently secured to the outer layer 11, preferably by stitching or sewing. Adhesive bonding or any other suitable means to join together two or more fabric layers can be used.

Figure 9:
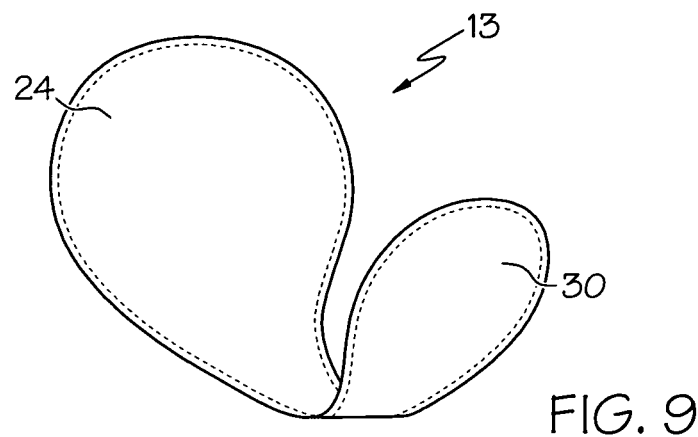
FIG. 9 is a frontal perspective view of the main absorbent layer isolated from the undergarment of FIG. 1.
Figure 10:
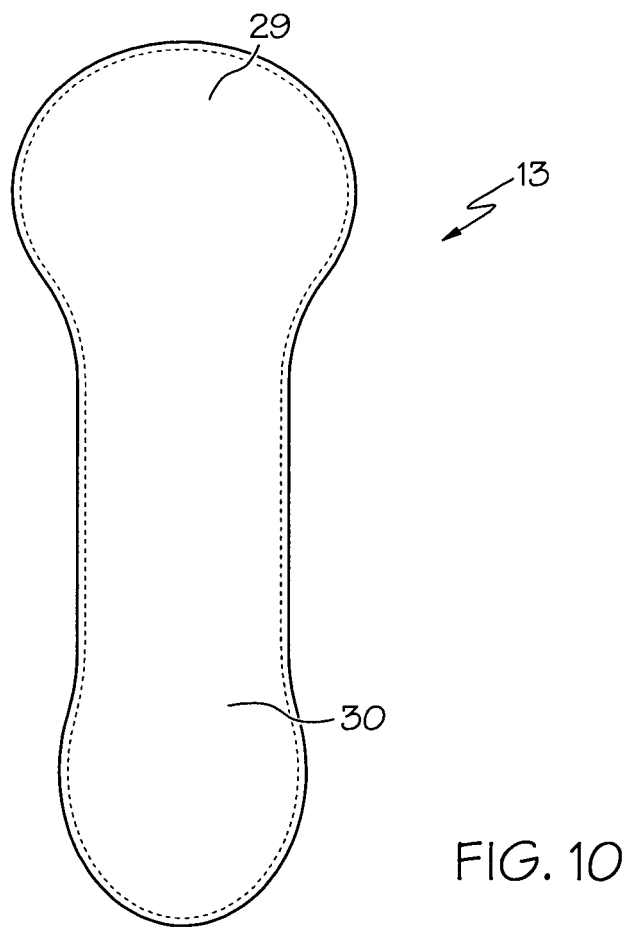
FIG. 10 is a top view of the main absorbent layer of FIG. 9.

The main absorbent layer 13 provides the principal means to catch any leakage from the wearer. It is made of a highly absorbent material. It is typically a non-woven fibrous material which is ultra soft. Its thickness is determined by its absorbency. It is shaped to cover the wearer's pubic area and anal area. Preferably, and as seen in FIGS. 9 and 10, it has an elongated rounded shape with a greater back section 29 for covering the anal area and a lesser front section 30 centered and extending therefrom for covering the pubic area. It is shaped similarly to a sanitary napkin, but with a fanned-out back section to better ensure more surface area to trap any leakage even before it can reach the absorbent inner layer 12.

The main absorbent layer 13 is positioned between the outer and inner layers prior to their being secured together in the respective crotch areas. All three layers are then permanently secured to each. Stitching is preferred. The resultant undergarment is unitary as apparent from FIGS. 1 and 2.

The undergarment of the invention is reliable in alleviating leakage from the wearer whether pre-menstruation, post-menstruation or during menstruation when a sanitary napkin is used as the primary source of absorbency and the undergarment as the secondary source. The alleviation of leakage by the undergarment is primarily due to the main absorbent layer, but secondarily the absorbent inner layer as well as the outer layer with its inherent water-resistance and snug fit. The snug fit not only will help keep any sanitary napkin in place when present, it will also help to absorb any leakage in the event it becomes displaced. The undergarment is also physically comfortable to wear due to the soft inner layer and the firm fitting outer layer. It is also mentally comfortable due to the peace of mind which comes from wearing the undergarment due to its reliability in alleviating and even totally preventing leakage.

Optional features often included in conventional undergarments can be added if desired provided the benefits attained in this invention are not affected. For example, an elastic waistband at the waist opening can be stitched on. Decorative edging at the waist and/or leg openings is feasible. Further, the undergarment can be made into many different styles, including in addition to the preferred boy shorts style, classic briefs, hipsters, high cut briefs, and bikinis.

Having described the invention in its preferred embodiment, it should be clear that modifications can be made without departing from the spirit of the invention. It is not intended that the words used to describe the invention nor the drawings illustrating the same be limiting on the invention. It is intended that the invention only be limited by the scope of the appended claims.

I claim:

1. A washable female undergarment for alleviating leakage, said undergarment comprising:
   (a) an outer layer of a water-resistant multi-direction stretchable fabric cut to define an unbroken waist opening and two unbroken leg openings with a crotch part extending between the two leg openings;
   (b) an inner layer of a soft absorbent fabric shaped and sized to fit within the outer layer and permanently secured thereto; and
   (c) a main absorbent layer sized to overlie the crotch part and positioned between the outer layer and the inner layer and permanently secured to said layers,
whereby the undergarment provides a comfortable snug fitting with good skin feel and good leakage absorbency for a user's physical and mental comfort.

2. The washable female undergarment of claim 1 wherein the outer layer is made from a spandex fabric.

3. The washable female undergarment of claim 2 wherein the outer layer includes a front part and a back part.

4. The washable female undergarment of claim 3 wherein the outer and inner layers are cut to obtain a boy shorts style undergarment.

5. The washable female undergarment of claim 3 wherein the main absorbent layer has au elongated rounded shape and is positioned to cover the crotch part of the outer layer.

6. A washable female undergarment of claim 5 wherein the main absorbent layer comprises a greater back section and a lesser front section centered and extending therefrom.

7. The washable female undergarment of claim 1 wherein the inner layer is made from a cotton fabric.

8. The washable female undergarment of claim 7 wherein the outer layer and the inner layer have substantially the same shape and size.

9. A slip-on washable female undergarment for alleviating leakage to outer clothing, bedding and elsewhere, said undergarment comprising:
   (a) an outer layer of a multi-direction stretchable fabric cut and stitched to define an unbroken waist opening and two unbroken leg openings with a front part, a back part and a crotch part extending between the two leg openings;
   (b) an inner layer of a soft absorbent fabric shaped and sized to substantially fit within the outer layer of multi-direction stretchable fabric and permanently secured thereto; and
   (c) a main absorbent layer sized to overlie the crotch part and positioned between the outer layer of multi-direction stretchable fabric and the inner layer of soft absorbent fabric and permanently secured to said outer and inner layers,
whereby the undergarment is unitary and provides a comfortable snug fitting with good skin feel and good leakage absorbency for a user's physical and mental comfort.

10. The washable female undergarment of claim 9 wherein the multi-direction stretchable fabric of the outer layer is a spandex fabric and the soft absorbent material of the inner layer is a cotton fabric.

11. The washable female undergarment of claim 10 wherein the main absorbent layer has an elongated rounded shape and is positioned to cover the crotch part of the outer layer.

12. The washable female undergarment of claim 11 wherein the main absorbent layer comprises a greater back section and a lesser front section centered and extending therefrom.

13. The washable female undergarment of claim 9 wherein the outer layer and the inner layer have substantially the same shape and size.

14. The washable female undergarment of claim 9 wherein the outer and inner layers are cut to obtain a boy shorts style undergarment wherein leg sections extends from about one inch to about two inches from the front and back parts.

15. A slip-on unitary washable female undergarment for alleviating leakage to an outer clothing, bedding and elsewhere, said undergarment comprising:
   (a) an outer layer of a spandex fabric cut and stitched to define a an unbroken waist opening and two unbroken leg openings with a front part, a back part, extended leg sections, and a crotch part;
   (b) an inner layer of a cotton fabric having substantially the same shape and size as the outer layer of spandex fabric and permanently secured therewithin; and
   (c) a main absorbent layer having an elongated rounded shape with a greater back section and a lesser front section, said main absorbent layer positioned between the outer layer of spandex fabric and the inner layer of cotton fabric and permanently secured to said outer and inner layers to form the unitary washable female undergarment, whereby the undergarment provides a comfortable snug fitting with good skin feel and good leakage absorbency for a user's physical and mental comfort.

* * * * *